United States Patent
Hauck et al.

(10) Patent No.: US 7,132,053 B2
(45) Date of Patent: Nov. 7, 2006

(54) PROTECTIVE DEVICE FOR THE CHROMATOGRAPHIC BED IN DYNAMIC AXIAL COMPRESSION CHROMATOGRAPHIC COLUMNS

(75) Inventors: Wilhelm Hauck, Media, PA (US);
Harlene Marks, Wallingford, PA (US);
Jean Blehaut, Swarthmore, PA (US);
Roger-Marc Nicoud, Lay-St-Christophe (FR)

(73) Assignee: Novasep, Pompey (FR)

( * ) Notice: Subject to any disclaimer, the term of this patent is extended or adjusted under 35 U.S.C. 154(b) by 0 days.

(21) Appl. No.: 10/474,622

(22) PCT Filed: Apr. 9, 2002

(86) PCT No.: PCT/FR02/01223

§ 371 (c)(1),
(2), (4) Date: Oct. 10, 2003

(87) PCT Pub. No.: WO02/084275

PCT Pub. Date: Oct. 24, 2002

(65) Prior Publication Data

US 2004/0099604 A1    May 27, 2004

(30) Foreign Application Priority Data

Apr. 1, 2001    (FR) .................................... 01 04866

(51) Int. Cl.
*B01D 15/08* (2006.01)
(52) U.S. Cl. .................................... 210/656; 210/198.2
(58) Field of Classification Search ............... 210/656, 210/659, 198.2, 137, 143; 96/101; 95/82
See application file for complete search history.

(56) References Cited

U.S. PATENT DOCUMENTS

| | | | | |
|---|---|---|---|---|
| 3,487,938 A | * | 1/1970 | Patterson | 210/198.2 |
| 3,966,609 A | | 6/1976 | Godbille et al. | |
| 4,043,906 A | * | 8/1977 | Helmer | 210/659 |
| 4,597,866 A | * | 7/1986 | Couillard | 210/198.2 |
| 4,769,141 A | | 9/1988 | Couillard | |
| 4,927,531 A | | 5/1990 | Sakamoto | |
| 5,044,203 A | * | 9/1991 | Wiest et al. | 73/730 |
| 5,158,676 A | | 10/1992 | Kreher et al. | |
| 5,485,724 A | * | 1/1996 | Nozawa et al. | 60/421 |
| 5,560,340 A | * | 10/1996 | Tomisawa | 123/494 |
| 5,667,675 A | | 9/1997 | Hatch et al. | |
| 5,919,361 A | | 7/1999 | Moran | |
| 6,843,918 B1 | * | 1/2005 | Hauck et al. | 210/656 |

FOREIGN PATENT DOCUMENTS

| | | |
|---|---|---|
| EP | 0 145 578 A2 | 6/1985 |
| FR | 2 219 797 | 9/1974 |
| FR | 2 556 099 A1 | 6/1985 |
| FR | 2 573 532 | 5/1986 |

\* cited by examiner

Primary Examiner—Ernest G. Therkorn

(57) ABSTRACT

The invention concerns a chromatographic device including a column (12) for receiving a chromatographic bed (14) through which flow a first fluid; a piston (36) sliding inside the column (12) an exerting pressure on the bed (14), a chamber (28) containing a second fluid exerting pressure on the piston (36); a regulator (52) for the pressure exerted by the piston (36) on the bed based on the pressure inside the chamber (28), on the flow pressure on the first fluid at the intake of the column (12) and on a reference pressure of the bed (14). Said device enables to separate at least two compounds to be subjected to chromatographic analysis, while adjusting the pressure exerted on the chromatographic bed. The device efficiently uses the chromatographic bed while protecting it.

11 Claims, 1 Drawing Sheet

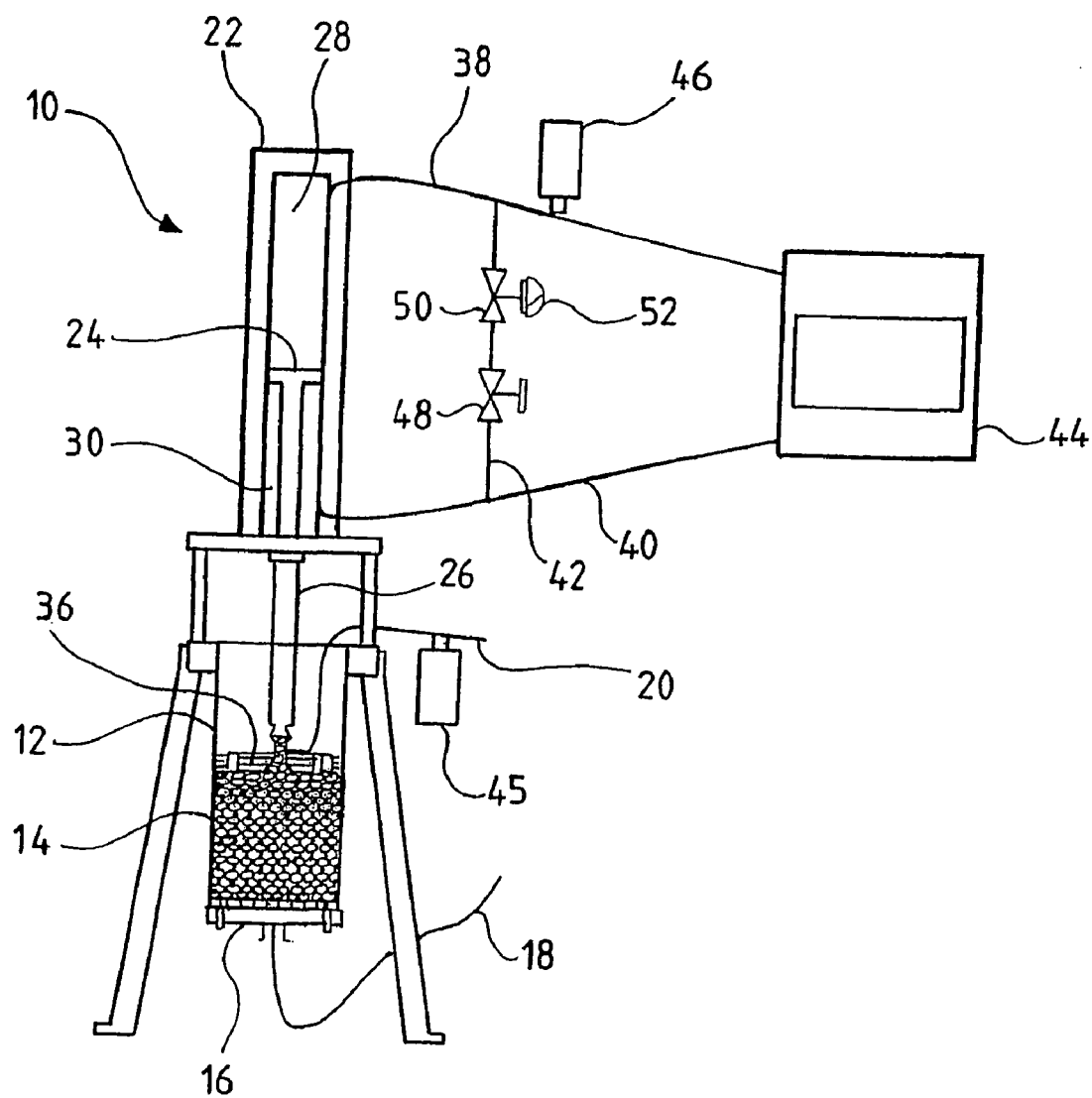

PROTECTIVE DEVICE FOR THE CHROMATOGRAPHIC BED IN DYNAMIC AXIAL COMPRESSION CHROMATOGRAPHIC COLUMNS

REFERENCE TO RELATED APPLICATIONS

This application is a 371 of PCT/FR02/01223 filed Apr. 9, 2002.

FIELD OF THE INVENTION

The present invention relates to the protection of the chromatographic bed of chromatographic columns and in particular in dynamic axial compression columns.

TECHNOLOGICAL BACKGROUND

In a process of separation by chromatography, the efficiency of the column used is a key parameter. The column is generally filled with a solid product in the form of very fine grains usually of a size comprised between 5 and 100 μm, forming the chromatographic bed. In order to obtain increased efficiency, the arrangement of the grains inside the column must be as homogenous as possible, and, moreover, empty volumes between the chromatographic bed and the column inlets-outlets must be avoided. It is known in the prior art, to resort to dynamic axial compression columns in order to ensure the existence of a compact bed, without free space between the inlet-outlet distributors and the bed.

Thus, from the French Patent Application FR-A-2 219 797, a chromatographic device is known, being presented in the form of a column intended to contain a bed of adsorbent material. The device is constituted by a tube comprising a lid and a element sliding in the tube, allowing a pressure to be exerted in the tube. The sliding element is a piston comprising at its head a porous plate which is permeable to fluids. In order to obtain the bed intended for chromatography, a suspension of particles of material capable of constituting an adsorbent bed is introduced into the tube with its lid removed, the piston being moved back sufficiently to allow the introduction of the suspension, without necessarily being at the dead centre. The lid is fitted to the tube, then a pressure is exerted on said suspension by means of the piston. The fluid is forced back through the porous plates, and said particles are compressed between the piston and the lid. This device makes it possible to achieve, in one embodiment, the compression stage of the chosen bed, and the desired compression of the particles when the sliding element has travelled ⅔ of the height of the column.

This device however has the disadvantage of inaccurate compression of the bed, since it is evaluated only by the position of the piston along the tube.

Also known from the European Patent Application EP-A-0 145 578, under priority of the Applications FR-A-2 556 099 and FR-A-2 573 532, is a chromatographic device comprising a tube, one part of which is intended to contain an adsorbent bed. This tube comprises two end walls and a piston sliding longitudinally in the tube. The piston marks, between the two end walls, a separation between one chromatographic chamber containing the bed and an enclosure in which a pressure prevails, such as to move the piston along the tube. The special feature of this device is that the fluid contained in the enclosure is liquid to be chromatographed diverted from the input conduit of the latter. Part of the liquid is diverted towards the enclosure via an enclosure conduit and the other part of the fluid is carried along to the chromatographic chamber via a flow conduit crossing the enclosure and the piston. When the piston is in the equilibrium position, the force exerted from the enclosure side on the piston is equal to the sum of the force on the piston produced by the flow of the liquid into the chamber to be chromatographed, and the mechanical force of the bed on the piston.

This device makes it possible, apart from carrying out the elution stage, to define the pressure exerted on the bed.

In a first embodiment, the piston has a constant section but the pressure in the flow and enclosure conduits is controlled by flap valves. Thus the valves can be calibrated such that the difference between the pressures exerted by the flow of the liquid and by the liquid in the enclosure are adjusted to a set-point pressure on the bed.

In another embodiment, the pressure in the flow and the enclosure conduits is the same, but the piston section varies. The piston is in two sections sliding in corresponding bores, the smaller section A being situated on the chromatographic chamber side and the larger section B on the enclosure side. Due to the difference in the areas of the piston surfaces A and B, the force exerted at B is greater than the force exerted at A. The piston sections can thus be chosen so that the difference between the pressures exerted by the flow of the liquid and by the liquid in the enclosure is adjusted to a set-point pressure on the bed.

In fact, the device described in the above document has various disadvantages. If a drop in pressure occurs in the flow conduit, the pressure exerted on the piston by the liquid in the enclosure is applied directly to the bed, which can give rise to deterioration of the bed. Moreover, the movements of the chromatographic bed not being monitored and the enclosure not being able to move back liquid during the chromatography, this device cannot adjust the pressure exerted on the bed as a function of the movements of the latter. A deterioration of the bed can again result. On the other hand, this system cannot be used in an SMB (Simulated Moving Bed) or VARICOL. In such configurations, the chromatographic devices are mounted in a loop and the liquids injected into the beds alternate. In the device described in EP-A-0 145 578, the same liquid is sent into the bed and into the enclosure, the alternation of injection of liquids gives rise to a mixture of these.

SUMMARY OF THE INVENTION

The object of the present invention is an improved chromatographic device making it possible to remedy the disadvantages of known devices. This device makes it possible to increase the efficiency of the chromatographic bed, whilst protecting it.

The present invention relates to a chromatographic device comprising:
- a column intended to receive a chromatographic bed through which a first fluid flows,
- a piston sliding in the column and exerting a pressure on the bed,
- a chamber containing a second fluid exerting a pressure on the piston,
- a regulator of the pressure exerted by the piston on the bed as a function of the pressure in the chamber, the flow pressure of the first fluid at the column inlet and a set-point pressure on the bed.

The regulator has a Proportional-Integral (PI) action, a Proportional-Differential (PD) action, or Proportional-Integral-Differential (PID) action.

The device moreover comprises a first sensor which measures the flow pressure of the first fluid at the column inlet and a second sensor which measures the pressure in the chamber.

In one embodiment, the first fluid flows through the bed from the piston in the direction of the end of the column.

In another embodiment, the first fluid flows through the bed from the end of the column in the direction of the piston.

The piston sliding in the column is linked to another piston sliding in the chamber by a rod.

In one embodiment, the second fluid is regulated by diversion by the regulator.

The invention also proposes a set of devices as described above, combined in a loop.

The invention also relates to a process for separating at least two compounds of a first fluid, comprising the chromatography of said fluid in the device described above, the process comprises the following stages:

introduction of the first fluid into the column containing the bed and measurement of the flow pressure at the inlet of the latter, flow of the first fluid through the chromatographic bed, collection of the first fluid chromatographed.

With the device according to the invention, it is possible, during the separation process, to carry out the stages:

introduction of a second fluid into the chamber and measurement of the pressure.

regulation of the pressure in the chamber as a function of the pressure measured in the chamber, the flow pressure of the first fluid at the column inlet and a set-point pressure on the bed.

The invention also relates to a process for regulating the pressure on the chromatographic bed in the device described above, the process comprising the stage:

regulation of the pressure in the chamber as a function of the pressure measured in the chamber, the flow pressure of the first fluid at the column inlet and a set-point pressure on the bed.

The regulation of the pressure exerted on the bed makes it possible to benefit from all its effectiveness whilst protecting it from degradation.

BRIEF DESCRIPTION OF THE DRAWINGS

Other characteristics and advantages of the invention will appear on reading the following detailed description of the embodiments of the invention, given by way of example only, and referring to the drawing which diagrammatically represents:

FIG. 1, an axial section of a chromatographic device according to the invention.

DESCRIPTION OF THE INVENTION

Reference is made to liquid chromatography, by way of illustration, which a person skilled in the art will easily transpose to gas chromatography without exceeding the scope of the invention. Similarly, this device is suitable for supercritical fluid chromatography.

FIG. 1 diagrammatically represents a chromatographic device 10 comprising a column 12 for carrying out the chromatography, and one part of which is intended to contain a chromatographic bed 14 resting on an end wall 16. Above the column 12, the device 10 also comprises a cylinder 22. The cylinder 22 comprises a mobile piston 24, connected to one end of a rod 26. The piston 24 delimits two chambers 28 and 30 in the cylinder 22. The first chamber 28, or upper chamber, is delimited between the piston 24 and the top wall 32 of the cylinder 22. The second chamber 30, or lower chamber, is delimited between the piston 24 and the lower wall 34 of the cylinder 22. The lower wall 34 marks the separation between the cylinder 22 and the column 12. The rod 26 connected to the piston 24 is situated in the lower chamber 30, and emerges in the column 12, by passing through the lower wall 34 of the cylinder 22. Appropriate joints are used to ensure water tightness between the chamber 30 and the column 12. The other end of the rod 26 situated in the column 12, is connected to an element 36. The element 36 slides in the column 12. The sliding element 36 is for example a piston. It is supported on the chromatographic bed 14.

The position of the cylinder 22 with respect to the column 12 is not limited to that described previously. It is in fact possible to envisage arranging the cylinder below the column such that the piston 36 is pressed upwards against the bed 14.

The liquid to be chromatographed is conveyed towards the bed 14 and is moved back from it by flexible conduits communicating towards the outside. The piston 36 comprises a conduit 20 equipped with a first flow pressure sensor 45. The wall 16 also has a conduit 18. The liquid to be chromatographed arrives at the bed 14 via the conduit 20, then leaves again via the conduit 18, after passing into the bed 14. The sensor 45 makes it possible to measure the fluid flow pressure at the inlet to the column 12.

The liquid to be chromatographed can also circulate in the other direction. It then arrives at the column 12 via the conduit 18, flows through the bed 14, then back out of the column 12 via the conduit 20. The sensor 45 is arranged on the inlet conduit 18.

The cylinder 22 is fed by a propellant-fluid circuit. Typically, the cylinder 22 is a double-acting hydraulic cylinder. The propellant fluid is then a hydraulic fluid. A first conduit 38 connects the chamber 28 with a source of hydraulic fluid 44. The conduit 38 comprises a second pressure sensor 46. A second conduit 40 connects the lower chamber 30 with the source of hydraulic fluid 44. A shunting conduit 42 links the conduits 38 and 40. The shunting conduit 42 comprises means of regulating the flow of propellant liquid into the diversion. These means comprise an all-or-nothing (AON) valve 48 and a control valve 50. The control valve is controlled by a regulator 52 of the Proportional Integral (PI) action type, Proportional Differential (PD) action type, or Proportional Integral Differential (PID) action type.

The liquids used in the device are distinct fluids. The first fluid, i.e. the gas or liquid to be chromatographed, is not the same as the propellant fluid, or second fluid, used in the cylinder 22. In other words, there is no diversion into the conduits of the first fluid in order to feed the cylinder 22.

The operation of the device will now be explained.

The device is used in a descent mode of the piston 36 in order to compress the chromatographic bed 14 in the column 12. The column 12 is filled in advance with the material forming the bed 14. The hydraulic fluid is then sent into the chamber 28 of the cylinder 22, in order to move the piston 36 down in the column 12 until the piston 36 comes into contact with the bed 14 and ensures its compression. In this case, the AON valve 48 and the control valve 50 are closed.

At the end of separation, the device allows the piston 36 to move back up in order to empty the bed 14 from the column 12. The hydraulic fluid is sent into the chamber 30 of the cylinder 22 in order to move the piston 36 back up. In this case the AON valve 48 and the control valve 50 are also closed.

The device is used for the separation of at least two compounds of a liquid to be chromatographed. The process comprises the stages:

introduction of the liquid to be chromatographed into the column 12 containing the bed 14. The liquid is for example introduced by the flexible conduit 20.

flow of the liquid through the bed 14. Depending on the affinities of the compounds with the bed 14, the compounds flow at different rates along the bed 14.

collection of the liquid chromatographed. The liquid compounds are separated and collected in the flexible conduit 18.

The separation of the compounds is accompanied by the regulation of the pressure exerted on the bed 14.

When the piston 36 is static, the different forces exerted on the piston are in equilibrium. The different forces are the hydraulic force (Hf) provided by the hydraulic source to the piston 36 compensated by the flow force (Ff) of the liquid to be chromatographed at the inlet to the column 12 and by the mechanical force of the bed (Bf). The mechanical force of the bed is thus given by the balance of the forces.

$$Bf = Hf - Ff \qquad \text{Eq. 1}$$

Conversion of the balance of the forces into a balance of the pressures leads to:

$$Bp = Hp.A1/A2 - Fp \qquad \text{Eq. 2}$$

where A1 is the surface of the piston 36 in the column 12 and A2 is the surface of the piston 24 in the chamber 28.

During the use of a chromatographic device, an abrupt stop of the flow of the liquid to be chromatographed can occur, for example during an emergency stop. The flow force (Ff) then becomes zero and all the hydraulic force Hf is exerted on the bed, resulting in Bf=Hf. If the mechanical resistance of the bed is average (for example if the bed is of silica with large pore diameters), the latter risks undergoing undesired compression, or even being damaged by the piston 36. Similarly, during use, the bed can expand to the point of no longer being firmly pressed against the piston. It is then necessary for the piston 36 to follow the bed in its movements.

Depending on the conditions under which the chromatography is carried out (the liquid to be chromatographed, flow rate in the bed etc.) and the characteristics of the bed used (material used, porosity, mechanical resistance etc.), it is possible to determine a set-point pressure (Rp) exerted on the bed. The hydraulic pressure Hp must be calculated as a function of the flow pressure, in order to verify:

$$Hp = (Rp + Fp).A1/A2 \qquad \text{Eq. 3}$$

When the flow pressure Fp varies, equation 3 shows that Bp can be maintained constant at the value of Rp by varying Hp. In order to do this, the hydraulic pressure Hp and the flow pressure Fp at the inlet to the column 12 must be measured. The use of a regulator 52 of the PI, PD, PID type makes it possible to regulate the pressure on the bed 14 according to the stages:

programming of a set-point pressure on the bed;

introduction of the liquid to be chromatographed into the column 12 which contains the bed 14 and measurement of the flow pressure of the liquid by the sensor 45 at the inlet to the column 12;

flow of the liquid through the bed 14;

introduction of the hydraulic fluid into the chamber 28 and measurement of the hydraulic pressure supplied to the cylinder 22 by the sensor 46;

comparison according to a regulation algorithm of the three abovementioned pressures;

regulation of the pressure in the chamber 28 as a function of the pressure measured in the chamber 28, of the flow pressure of the liquid to be chromatographed at the inlet to the column 12 and of the set-point pressure on the bed.

The separation process can then be completed by the stage of introduction of the hydraulic fluid into the chamber 28 and the stage of regulation of the pressure in the chamber 28.

By way of illustration, when the flow of the liquid to be chromatographed is stopped, the flow pressure drops to zero. With equation 3, it is deduced that the hydraulic pressure must be reduced in order to attain Hp=Rp.A2/A1. In order to achieve this, the regulator 52 diverts the hydraulic fluid into the shunting conduit 42 by opening the AON valve 48 and by opening the control valve 50 to a percentage controlled by the regulator 52. The hydraulic fluid sent by the hydraulic source 44 does not penetrate into the chamber 28 but is diverted into the shunting conduit 42. It is then evacuated towards the hydraulic source 44. In this manner, the pressure in the chamber 28 is reduced, resulting in a lower pressure of the piston 36 on the bed 14.

The regulation of the pressure exerted by the piston 36 on the bed 14 makes it possible to adapt to the movements of the bed 14 when the latter expands, for example. The increase in the volume of the bed 14 would result in an increase in the mechanical pressure of the bed Bp, which would become greater than the set-point pressure Rp. In a standard implementation of the cylinder 22, the hydraulic fluid cannot leave the upper chamber 28 of the cylinder 22, and an increase in the pressure Bp would result in an increase in the hydraulic pressure. It is therefore necessary in this case to evacuate the hydraulic fluid from the chamber 28 in order to keep Bp constant. Once again the AON valve 48 is opened and the control valve 50 is opened to a percentage controlled by the regulator 52, making it possible to keep the pressure Bp constant and equal to Rp.

The regulation of the pressure of the piston 36 on the bed 14 makes it possible to adjust to the device's operating conditions. It allows all the efficiency of the bed 14 to be available, whilst protecting it.

The device described above is not limited to a single piston compressing the bed 14 but it is possible to envisage the action of two pistons on the bed 14. On the other hand, a person skilled in the art will be able to use other types of cylinders such as a pneumatic cylinder.

The chromatographic device according to the invention is advantageously used in an SMB (Simulated Moving Bed) separation process (U.S. Pat. Nos. 2,985,589, 3,291,726, 3,268,605 and U.S. Pat. No. 3,266,604 belonging to UOP, U.S. Pat. No. 5,578,215 U.S. Pat. No. 5,578,216 belonging to IFP and NOVASEP, EP 471 082 and EP 563 388 belonging to DAICEL) or in a VARICOL process (U.S. Pat. No. 6,136,198). Such a process uses a set of these columns combined in a loop.

The invention claimed is:

1. A process for separating at least two compounds in a first fluid, said process comprising subjecting said fluid to chromatography in a chromatographic device, by:

flowing said first fluid through a column (12) containing a chromatographic bed (14), exerting a pressure on the bed (14) by a piston (36) sliding in the column (12), exerting a pressure on the piston (36), by a chamber (28) containing a second fluid, regulating the pressure exerted by the piston (36) on the bed (14) as a function of the pressure in the chamber (28), the flow pressure of the first fluid at the inlet to the column (12) and a set-point pressure on the bed (14), the regulation of the pressure exerted by the piston on the bed comprising the reduction of the pressure in the chamber if the pressure on the bed is greater than the set point pressure on the bed and collecting the first fluid chromatographed.

2. The process of claim 1, comprising regulating the pressure exerted by the piston on the bed (36) by keeping the pressure constant and equal to the set-point pressure on the bed.

3. The process of claim 2, wherein the set-point pressure on the bed is selected based on the conditions under which the chromatography is carried out, and on the characteristics of the bed.

4. The process of claim 3, wherein the first fluid flows through the bed (14) from the piston (36) in the direction of the end (16) of the column (12).

5. The process of claim 3, wherein the first fluid flows through the bed (14) from the end (16) of the column (12) in the direction of the piston (36).

6. The process of claim 3, wherein the pressure of the second fluid is regulated by diverting said fluid by a flow regulator (52).

7. The process of claim 1, wherein the pressure is regulated by a first sensor (45) measuring the flow pressure of the first fluid at the inlet to the column (12) and a second sensor (46) measuring the pressure in the chamber (28).

8. The process of claim 1, wherein the second fluid exerts pressure on a piston (24) sliding in the chamber (28) connected to a rod (26) actuating the piston (36), whereby the pressure is regulated.

9. A process for regulating the pressure on a chromatographic bed in a chromatographic device, said device comprising:

a column (12) intended to receive a chromatographic bed (14) through which a first fluid flows, the first fluid comprises at least two compounds to be separated, a piston (36) sliding in the column (12) and exerting a pressure on the bed (14), a chamber (28) containing a second fluid exerting a pressure on the piston (36), a regulator (52) of the pressure exerted by the piston (36) on the bed, said process comprising regulating the pressure in the chamber (28) as a function of the pressure measured in the chamber (28), the flow pressure of the first fluid at the inlet to the column (12) and a set-point pressure of the bed (14), the regulation of the pressure exerted by the piston on the bed comprising the reduction of the pressure in the chamber if the pressure on the bed is greater than the set point pressure on the bed.

10. The process of claim 9, wherein regulation of the pressure comprises keeping the pressure exerted by the piston on the bed constant and equal to the set-point pressure on the bed.

11. The process of claim 10, wherein the set-point pressure on the bed is pre-selected based on the conditions under which the chromatography is carried out, and on the characteristics of the bed.

* * * * *